(12) United States Patent
Jacobson et al.

(10) Patent No.: US 8,465,803 B2
(45) Date of Patent: Jun. 18, 2013

(54) TEMPLATED MONOLAYER POLYMERIZATION AND REPLICATION

(75) Inventors: Joseph M. Jacobson, Newton, MA (US); David W. Mosley, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/556,148

(22) Filed: Jul. 23, 2012

(65) Prior Publication Data
US 2012/0288626 A1 Nov. 15, 2012

Related U.S. Application Data

(60) Continuation of application No. 11/963,970, filed on Dec. 24, 2007, now Pat. No. 7,563,482, which is a division of application No. 10/621,897, filed on Jul. 17, 2003, now Pat. No. 7,311,943, application No. 13/556,148, filed on Jul. 23, 2012, which is a division of application No. 12/505,508, filed on Jul. 19, 2009, now Pat. No. 8,227,035.

(60) Provisional application No. 60/396,486, filed on Jul. 17, 2002.

(51) Int. Cl.
*B05D 3/00* (2006.01)
*B05D 1/18* (2006.01)

(52) U.S. Cl.
CPC ............. *B05D 1/185* (2013.01); *Y10S 977/882* (2013.01); *Y10S 977/883* (2013.01)
USPC ........... 427/258; 427/201; 427/202; 427/437; 427/443.1; 427/372.2; 977/882; 977/883; 438/478

(58) Field of Classification Search
CPC ...................................................... B05D 1/185
USPC ........ 427/180, 201, 202, 258, 372.2; 438/99, 438/478–509; 977/882, 883
See application file for complete search history.

*Primary Examiner* — William Phillip Fletcher, III
(74) *Attorney, Agent, or Firm* — Norma E. Henderson

(57) ABSTRACT

A self-replicating monolayer system employing polymerization of monomers or nanoparticle ensembles on a defined template provides synthesis of two-dimensional single molecule polymers. Systems of self-replicating monolayers are used as templates for growth of inorganic colloids. A preferred embodiment employs SAM-based replication, wherein an initial monolayer is patterned and used as a template for self-assembly of a second monolayer by molecular recognition. The second monolayer is polymerized in place and the monolayers are separated to form a replicate. Both may then function as templates for monolayer assemblies. A generic self-replicating monomer unit comprises a polymerizable moiety attached by methylene repeats to a recognition element and an ending unit that will not interfere with the chosen recognition chemistry. The recognition element is self-complementary, unless two replicating monomers with compatible cross-linking chemistry are employed. After replication, selective mineralization and/or electroless plating may produce a two-dimensional inorganic sheet having patterned domains within it.

20 Claims, 12 Drawing Sheets

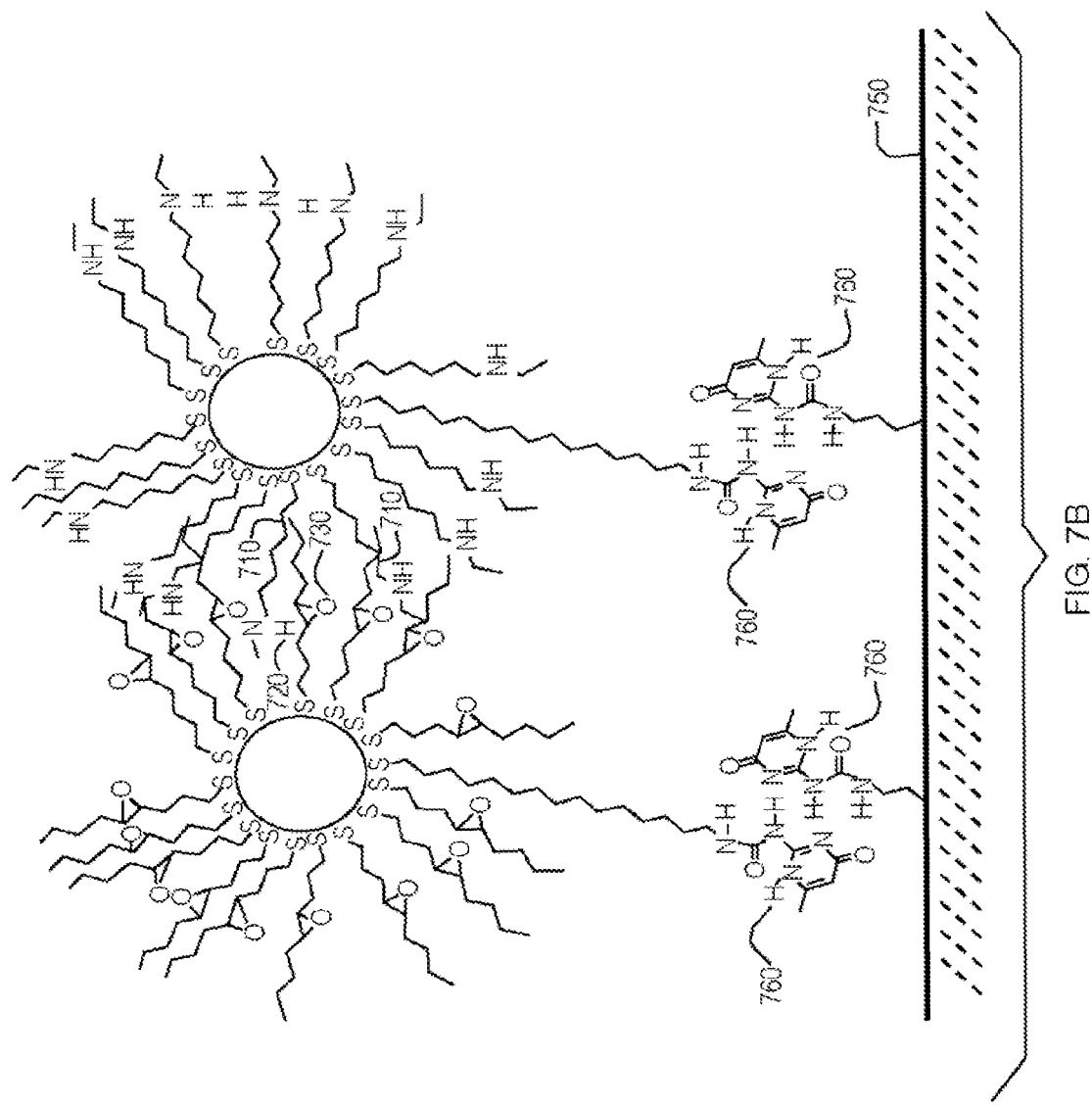

TEMPLATED MONOLAYER POLYMERIZATION AND REPLICATION

RELATED APPLICATIONS

This application is a divisional application of U.S. patent application Ser. No. 12/505,508, filed Jul. 19, 2009, now U.S. Pat. No. 8,227,035, issued Jul. 24, 2012, which is a continuation application of U.S. patent application Ser. No. 11/963,970, filed Dec. 24, 2007, now U.S. Pat. No. 7,563,482, issued Jul. 21, 2009, which is a divisional application of U.S. patent application Ser. No. 10/621,897, filed Jul. 17, 2003, now U.S. Pat. No. 7,311,943, issued Dec. 25, 2007, which claims the benefit of U.S. Provisional Application Ser. No. 60/396,486, filed Jul. 17, 2002, the entire disclosures of which are each herein incorporated by reference.

FIELD OF THE INVENTION

This invention relates to monolayer polymerization and, in particular, to self-replicating systems of monolayers and methods for polymerizing organic thin film monolayer assemblies.

BACKGROUND

As nanotechnology pushes forward, the need increases for reliable methods of producing discrete nanostructures, either organic or inorganic, of specific shape and size, particularly in the 2-1000 nm regime. Two general approaches exist for making nanostructures: from the bottom up through chemical synthesis and from the top down through lithographic methodology. Techniques that target the region between the current capabilities of these two technologies, i.e., from about 2 nm to about 1000 nm, are currently highly sought after.

Prior art nanostructure synthesis methods that have been developed include focused-ion beam milling, scanning probe techniques, and x-ray lithography. While advanced mask-based lithography techniques are capable of producing large quantities of structures of small size, they are typically very expensive. Although milling techniques and scanning probe techniques are somewhat more affordable, they are primarily useful for the production of very small numbers of nanostructures. Further, all these available techniques are generally deployed to produce structures that are directly attached to surfaces or are integral parts of a surface. There are no general methods to produce mole quantity ($6\times10^{23}$) amounts of nanostructures that are lithographically defined. Such large quantities of nanostructures are almost by necessity solution based, since they would otherwise occupy a very large amount of surface area.

Biological systems utilize templated replication to produce large quantities of nanostructures such as nucleotide chains and peptide chains. Nucleotide synthesis is based upon hydrogen bond templating, followed by polymerization. Attempts have therefore been made to mimic the efficiency of oligonucleotide synthesis for various kinds of polymers, typically via hydrogen-bonded assembly or electrostatic assembly.

In general, polymerization of monolayers has been extensively studied. Many different routes to achieve non-patterned polymerization of a single monolayer have been investigated. Of particular relevance are polymerization systems that are topochemical in nature. A topochemical polymerization typically results in very little rearrangement of the monolayer once polymerization has occurred.

The poly(diacetylene)s (PDAs) exemplify such a system. PDA polymerization in both a self-assembled monolayer and in a Langmuir-Blodgett (LB) monolayer on gold has been achieved. FIG. 1 depicts a prior art scheme of diacetylene polymerization on a gold substrate by attachment of functionalized alkyl thiols. Attempts have been made to use hydrogen bonding to control polymerization in Langmuir-Blodgett monolayers. Since PDAs are polymerized by UV light, extensions to lithographic production of monolayers are relatively straightforward.

PDAs have also been polymerized in covalently bonded multilayers of monolayers. A multilayer film can be produced by covalent linkages, with the number of layers being controlled by a sequence of steps. Multilayer films have also been generated using hydrogen bonding and coordination bonding. FIG. 2 depicts a prior art approach to synthesis of a multilayer film, wherein a second monolayer is grown on a gold-alkyl thiol self-assembled monolayer (SAM) via hydrogen bonding (amide recognition).

Replication of siloxane monolayers through several generations on a substrate has also been reported. The monolayers replicate through what is understood to be an acetone-assisted process, involving hydrogen bonding and solvent intercalation for separating the replicate from the template. The replication process is not a one-pot process, nor are the monolayers specifically cross-linked or patterned. The monolayers are attached to the surface of a silicon substrate, and replication stalls after 4-5 generations. A method of replicating monolayers that is highly controlled and can be used to replicate patterns over many generations would be highly desirable and has never been reported.

Large scale two-dimensional polymers have often been produced by Langmuir-Blodgett techniques (Palacin et al., *Thin Films* 20:69-82 (1995)). One instance of patterned polymer multilayers that are free of a surface has been reported (Stroock et al., *Langmuir* 19(6): 2466-2472 (2003)), however, synthesis of two-dimensional lithographically defined single molecule polymers that can be readily suspended in a solvent has not.

Electroless plating of metals onto organic molecules is a common technique in biology, often used for histology staining Electroless plating onto nanostructures has also been reported recently, using an amide template to coordinate metal ions as the electroless plating seeds (Matsui et al., *J. Phys. Chem. B* 104: 9576-79 (2000)). In addition, mineralization of organic structures is also a burgeoning field, and techniques for mineralizing $CaCO_3$ and $SiO_2$ are being developed and explored. Templating of semiconductor crystals has also been reported (Whaley S. R. et al., *Nature* 405: 665-668 (2000)).

Polymerization of nanoparticles has been reported in many ways. Typically, nanoparticles have been polymerized by using a polymerizable moiety in the ligand sphere of the nanoparticle (Boal et al., *Adv. Functional Mat.* 11(6): 461-465 (2001)), or by decorating a pre-existing polymer chain with nanoparticles (Walker et al., *J. Amer. Chem. Soc.* 123: 3846-3847 (2001)). Polymerization in films has been reported using dithiol chemistry (Musick et al., *Chem. Mater.* 12: 2869-2881 (2000)). Further, melting or agglomeration of nanoparticles into films is well known (U.S. Pat. No. 6,294,401, Ridley et al. (2001)). However, polymerization of a nanoparticle ensemble using a lithographically defined template has not been reported.

What has been needed, therefore, are techniques for making large quantities of nanostructures that target the region between the capabilities of current technology, i.e., from about 2 nm to about 1000 nm. In particular, what is needed is a method for synthesis of two-dimensional lithographically-defined single molecule polymers that can be readily suspended in a solvent, and may be further used to generate inorganic structures. What is further particularly needed is a method of replicating monolayers that is highly controlled and can be used to replicate patterns over many generations, preferably as a "one-pot" process producing monolayers that are specifically cross-linked or patterned.

SUMMARY

These and other objectives are met by the present invention, which combines monolayer replication, hydrogen-bonding, and topochemical polymerization in order to achieve a self-replicating monolayer system. The present invention features techniques that are particularly useful for the synthesis of nanostructures sized from about 2 nm to about 1000 nm. The method of the present invention is highly controllable, can be used to replicate patterns over many generations, and is a "one-pot" process producing monolayers that are specifically cross-linked or patterned. In one aspect, the apparatus and method of the present invention provide a self-replicating monolayer system through polymerization of a nanoparticle ensemble using a lithographically-defined template. The present invention further provides a method for synthesis of two-dimensional lithographically-defined single molecule polymers that can be readily suspended in a solvent.

The self-replicating system of the present invention may be implemented using lithography or other techniques known in the art. Once created, the monolayers are used as templates for the growth of inorganic colloids, such as colloids of metals, semiconductors, and insulators. In one aspect, the invention features systems of self-replicating monolayers. The systems include a group of components, each of which may be varied, with the combination of the components providing the self-replicating system.

A preferred embodiment of the present invention is a self-assembling monolayer (SAM)-based replication scheme. An initial monolayer is patterned and then used as a template for the self-assembly of a second monolayer by molecular recognition. The initial monolayer may optionally be polymerized, in order to provide better lattice matching and structural rigidity of the desired pattern. Once the second monolayer has formed through self-assembly, it is polymerized in place. The two monolayers are then separated through any suitable mechanism, forming a replicate of the original monolayer. Both the replicate and the original monolayer may now function as templates for monolayer assemblies, and the process can be repeated, forming an exponential replication system.

In a generic self-replicating monomer unit according to one embodiment of the present invention, an ending unit that will not interfere with the chosen recognition chemistry is attached by methylene repeats to a polymerizable moiety. The polymerizable moiety may be a single polymerizable unit, but preferably contains two polymerizable units separated by some number of methylenes. The polymerizable moiety is then attached by further methylene repeats to recognition chemistry based on any suitable chemistry. Whatever the choice for recognition chemistry, the template must display a complementary recognition element.

The recognition element must be self-complementary, unless there is a set of two replicating monomers. In an exemplary two-component replication system utilizing two different kinds of recognition chemistries, the initial template undergoes replication cycles, while maintaining the two-dimensional segregation of the two types of replicating monomers having compatible cross-linking chemistry. During subsequent replications, the component domains experience little or no mixing, allowing the two-component, patterned assembly to be exponentially replicated. After replication, selective mineralization and/or electroless plating may produce a two-dimensional inorganic sheet having patterned domains within it. In general, inorganic colloid growth may be achieved through appropriate reduction chemistry of the desired metal salts and the use of seed or template-mediated nucleation.

More than two chemically compatible molecules may be used in monolayer synthesis. Patterning of the initial template is accomplished according to the defined regions of the two or more molecules composing the monolayer. After replication is complete, the two component replicates may then be mineralized or electroless plated in a way that maintains the pattern of the replicants, creating opportunities for making two-component inorganic colloids that are patterned.

BRIEF DESCRIPTION OF THE DRAWINGS

FIGS. 7A-B illustrate two-component nanoparticle cross-linking and replication according to an embodiment of the present invention;

DETAILED DESCRIPTION

Figure 1:
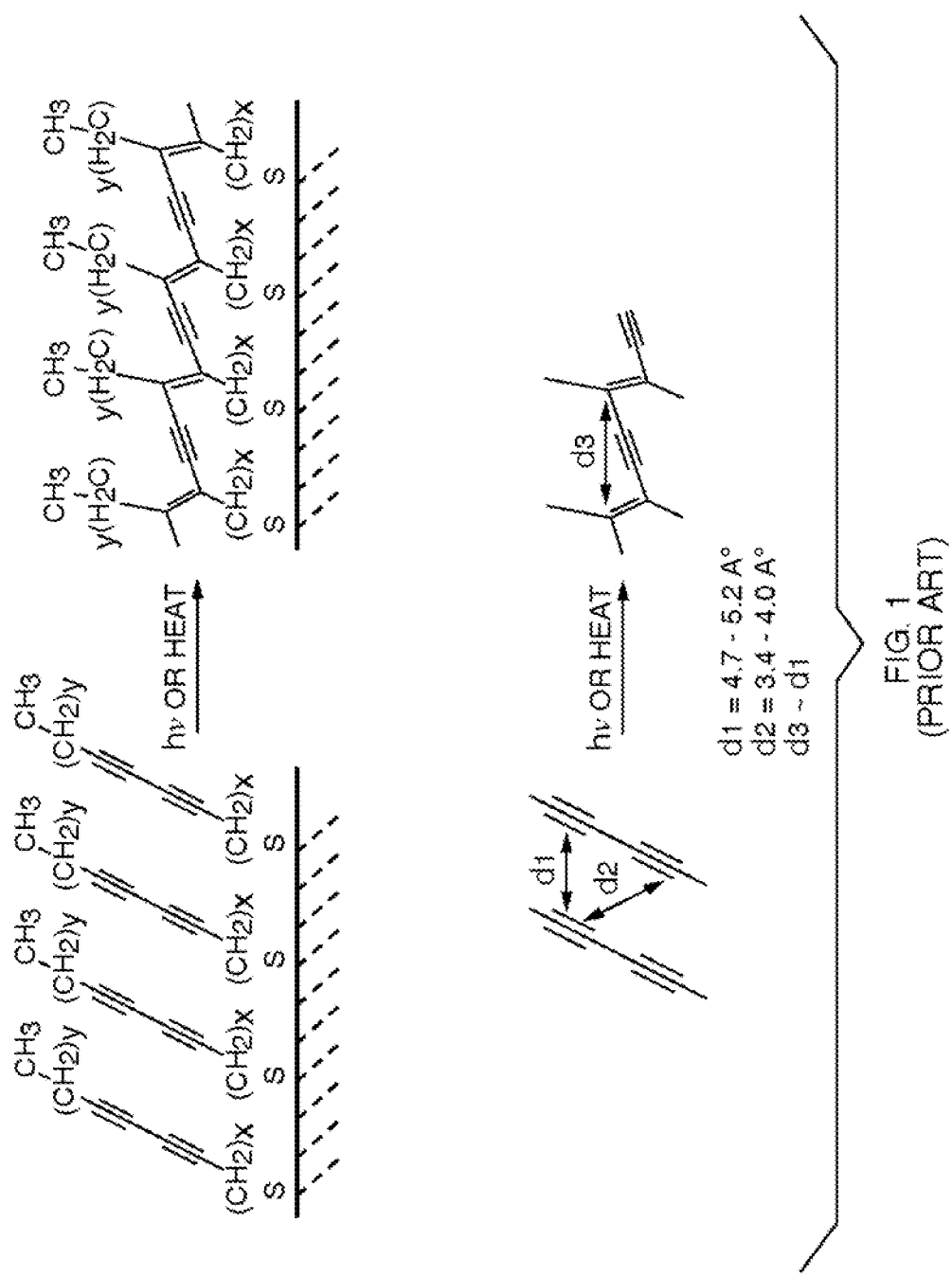
FIG. 1 depicts prior art diacetylene polymerization on a gold substrate by attachment of functionalized alkyl thiols.
Figure 2:
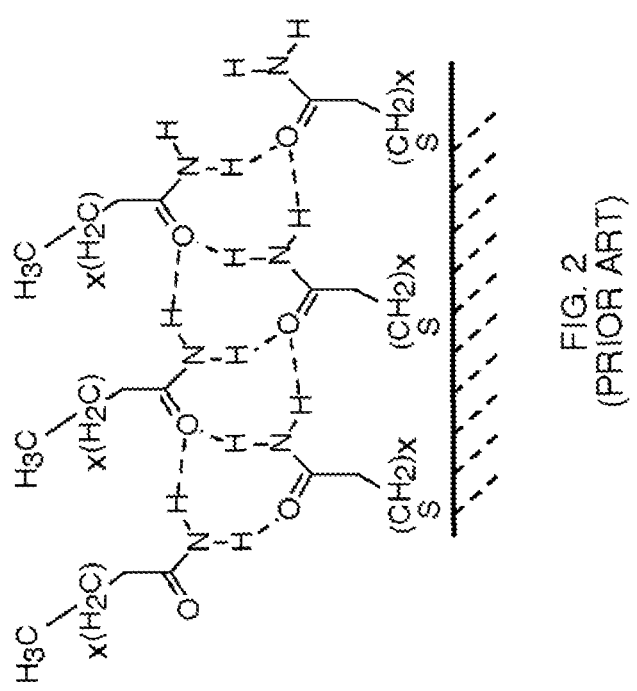
FIG. 2 depicts a prior art approach to synthesis of a multi-layer film, wherein a second monolayer is grown on a gold-alkyl thiol self-assembled monolayer via hydrogen bonding.

The present invention combines monolayer replication, hydrogen bonding, and topochemical polymerization in order to achieve a self-replicating monolayer system. The self-replicating system can be implemented using lithography or any other suitable technique known in the art. Once created, the monolayers are used as templates for the growth of inorganic colloids, such as colloids of metals, semiconductors, and insulators. In one aspect, the invention features systems of self-replicating monolayers. The systems include a group of components, each of which may be varied. The combination of the components provides the self-replicating system.

Polymerization.

In accordance with the present invention, polymerization techniques are utilized to effect polymer formation in the monolayer. A topochemical polymerization is typically preferred, although a non-topochemical polymerization may also be advantageously employed. A topochemical polymerization is preferable because it will generally cause the least perturbation of the monolayer conformation, either on a surface or in a solution. Also, a topochemical polymerization generally does not result in polymer formation by solution species, which can be important when a system is to be replicated many times.

Polymerizations by externally controllable means relative to the reaction mixture are preferred. Preferably, no additional reagents are used to cause polymerization. Particularly suitable polymerization methods include, but are not limited to, 'reagentless' polymerizations, such as where a polymerization reaction is catalyzed by heat, by electromagnetic radiation, or by particle radiation.

A two-dimensional, cross-linked polymer network is generally preferred, and can be produced from monomers with two or more reactive sites. Such cross-linked monolayers have been made using Langmuir-Blodgett (LB) monolayer techniques (Ahmed et al., *Thin Solid Films* 187: 141-153 (1990)). A cross-linked monolayer is typically more structurally robust.

The polymerization reactions and replication steps are typically carried out in a solvent. The solvent used to carry out replication is generally selected for its ability to solubilize the monolayer assemblies and the monomer feedstock.

Monomers and Monolayer.

The "monolayer basis" is the base monolayer system used to form patterns and serves as the initial template for replication. Monolayers can be formed as self-assembled monolayers (SAMs) on substrates (e.g., ultraflat surfaces), or as LB monolayers at, for example, the air-water interface.

Preferably, the monolayer template is created with as few defects as possible, making it as close to atomically smooth as possible. The monolayer basis should be patternable by one of the methods known in the art for two-dimensional patterning. Both SAMs and LB monolayers can be used. LB monolayers are readily prepared in atomically flat form, and maintain high ordering even during transfer to a substrate. SAM systems on gold typically exhibit a measurable roughness, even on ultraflat gold substrates, which may be due to the act of SAM creation itself in the gold/alkyl thiol system. However, small step heights on a surface often do not affect the chosen polymerization technique. Siloxane monolayers can also be prepared on ultraflat surfaces such as glass and silicon.

The monolayer basis, if it has an underlying set of lattice constants, should match the lattice constants and geometries required for the monolayer templating chemistry and the polymerization chemistry. In addition, the polymerization employed should result in a polymer with the requisite lattice constants and angles needed for formation of another monolayer after polymerization. For example, in a PDA system, the lattice spacing between monomers is about 4.9 angstroms in order for polymerization to occur. This lattice spacing should coincide with the lattice spacing necessary for monolayer packing on a SAM or in a LB film, as well as with the molecular recognition chemistry needed to assemble a multilayer film. In order for the system of the invention to successfully function as a self-replicating monolayer system, all these factors must be considered during selection of the ensemble of components.

The monomers used to form the replicating monolayers normally incorporate all the structural moieties necessary to effect the desired polymerization technique and/or monolayer formation technique, as well as to influence such properties as overall solubilities, dissociation methods, and lithographic methods. Many monomers can be designed for use in templated monolayer replication systems. The monomers typically contain at least one, and preferably two, reactive functional groups. The monomers also may contain a terminus bearing one or more molecular recognition elements, such as, but not limited to, carbonyl functionalities, heterocycles, and charged moieties. This terminus is used to guide assembly of the second monolayer prior to replication by polymerization. The monomers can also be designed to enhance colloidal solubility of the resulting monolayers.

The molecules used to form organic monolayers generally include various organic functional groups interspersed with chains of methylene groups. The molecules are typically long chain carbon structures containing methylene chains to facilitate packing. The packing between methylene groups allows weak Van der Waals bonding to occur, enhancing the stability of the films produced and counteracting the entropic penalties associated with forming an ordered phase. In addition, hydrogen-bonding moieties may be present at one terminus of the molecules, in order to allow templating of an adjacent monolayer, in which case the polymerizable chemical moieties are then placed in the middle of the chain or at the opposite terminus.

Figure 3A:
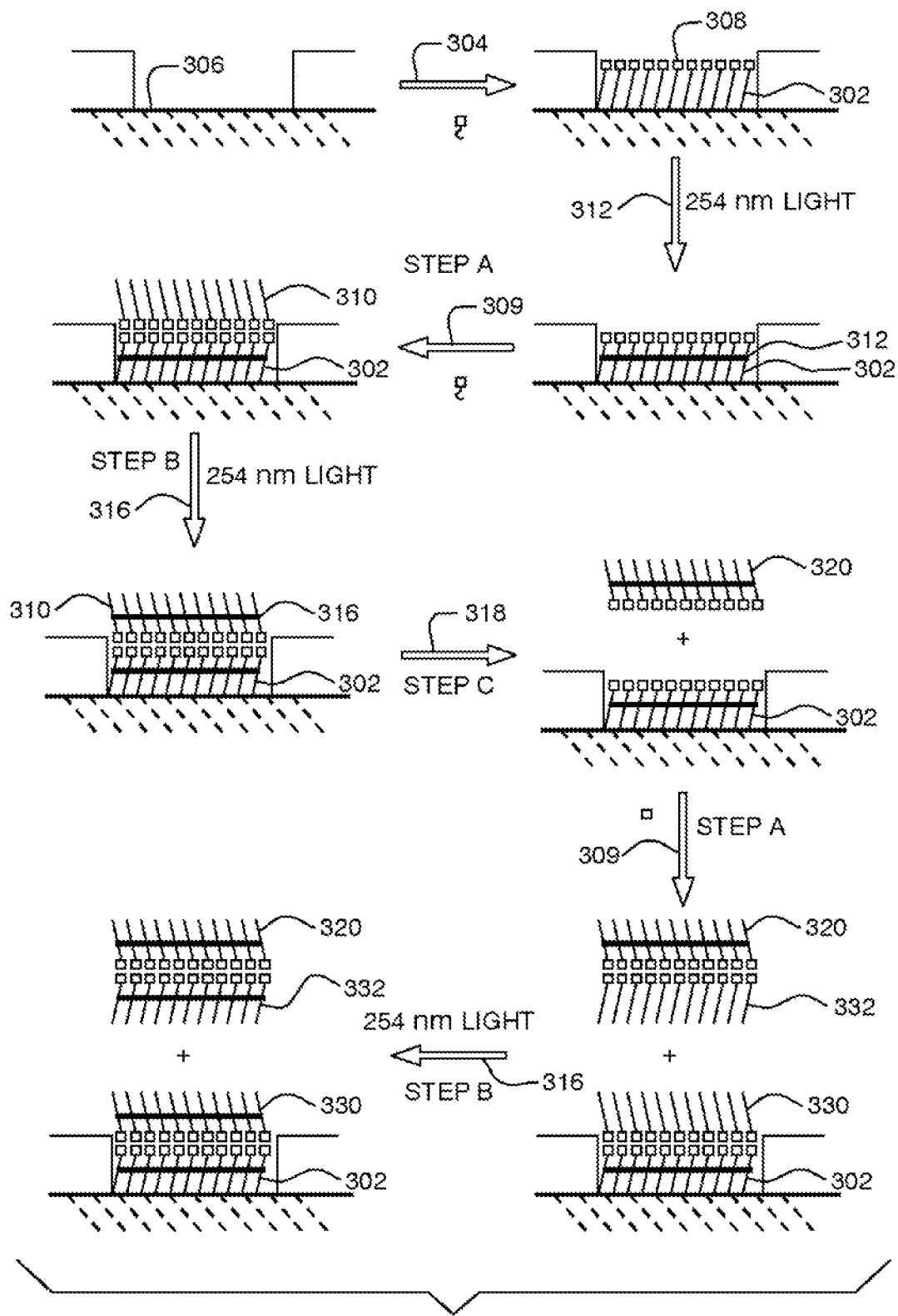
FIG. 3A illustrates the first part of a self-assembling monolayer (SAM)-based replication scheme according to an embodiment of the present invention.
Figure 3B:
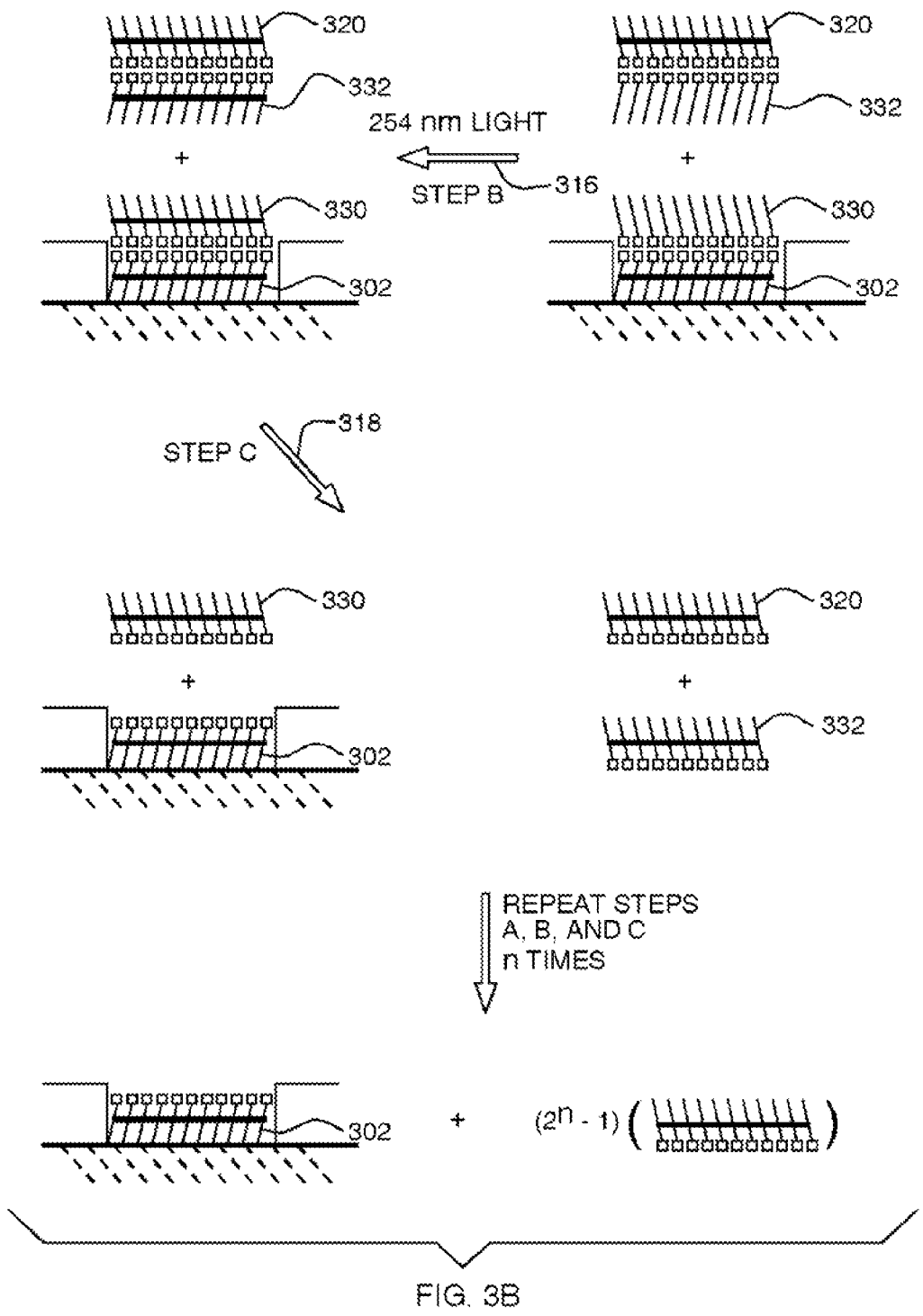
FIG. 3B illustrates the second part of a self-assembling monolayer (SAM)-based replication scheme according to an embodiment of the present invention.
Figure 4:
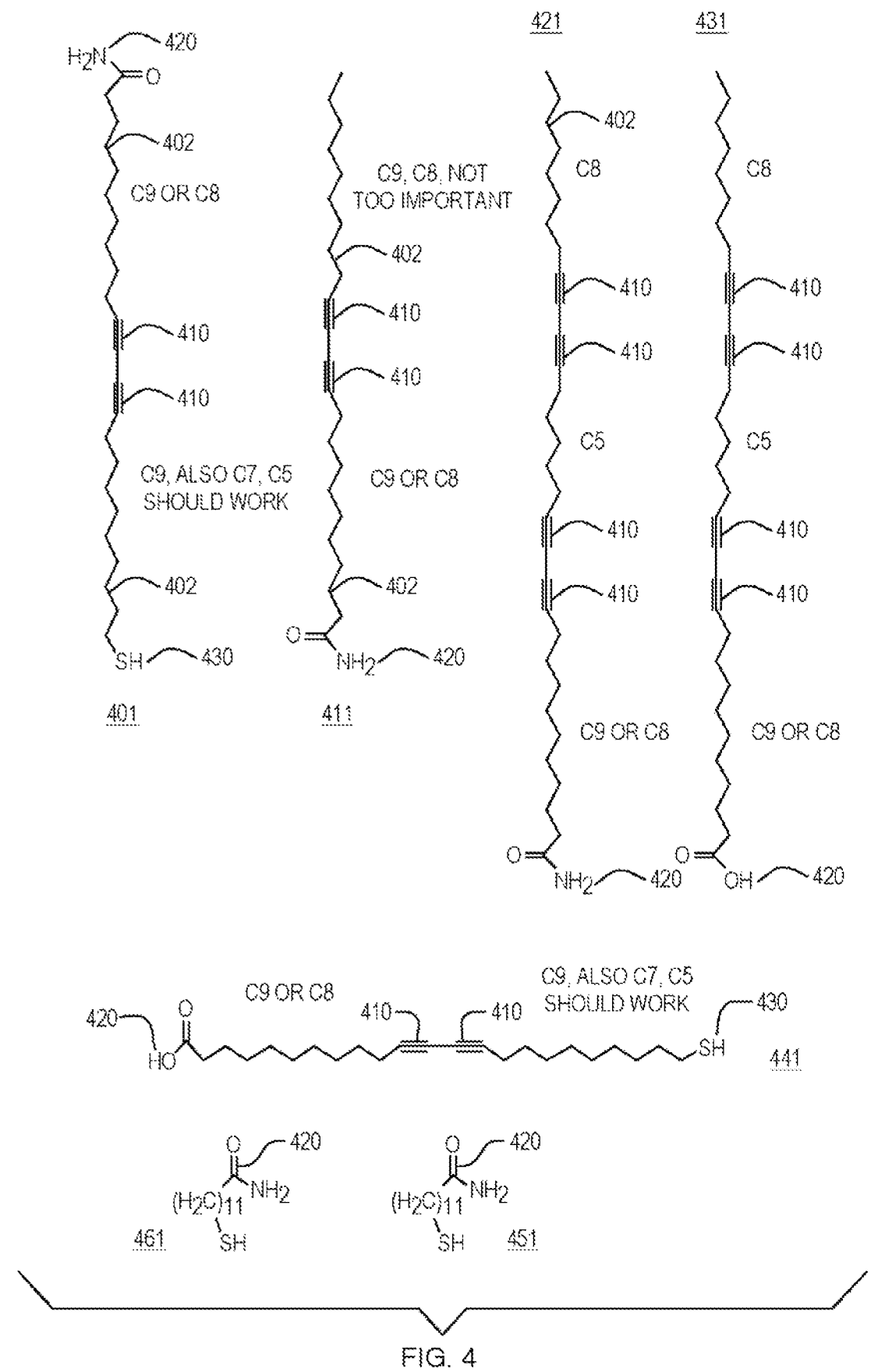
FIG. 4 depicts exemplary molecules that can be used in a SAM-based system according to an embodiment of the present invention.
Figure 5A:
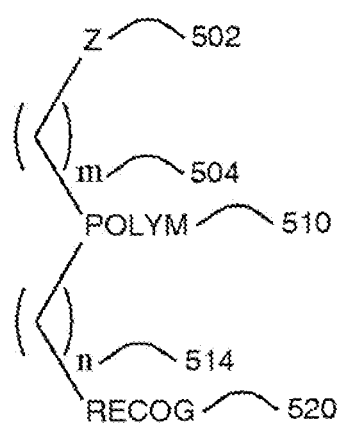
FIG. 5A depicts a generic self-replicating monomer unit utilized in an embodiment of the present invention.

As shown in FIGS. 3A and 3B, if a SAM-based system is used, an additional molecule is generally utilized to form the initial template. This additional molecule has appropriate functionality at one of its termini in order to form a SAM. For example, on a gold surface, a terminal thiol can be included. There are a wide variety of organic molecules that may be employed to effect replication. Topochemically polymerizable moieties, such as dienes and diacetylenes, are particularly desirable as the polymerizing components. These can be interspersed with variable lengths of methylene linkers. Exemplary target molecules that can be used in a SAM-based system are shown in FIG. 4. FIG. 5A depicts a generic organic monolayer replicating monomer.

For an LB monolayer system, only one monomer molecule is needed because the molecular recognition moiety can also serve as the polar functional group for LB formation purposes. Lithography can be carried out on a LB monolayer transferred to a substrate, or directly in the trough. For example, an LB monolayer of diacetylene monomers can be patterned by UV exposure through a mask or by electron beam patterning.

Monolayer formation can be facilitated by utilizing molecules that undergo a topochemical polymerization in the monolayer phase, but not in the solution or gas phase. By exposing the assembling film to a polymerization catalyst, the film can be grown in situ, and changed from a dynamic molecular assembly to a more robust polymerized assembly.

Since polymerization only occurs in the monolayer, monolayer formation can be promoted by exposure to UV light or polymerization catalysts. The inherent stresses and surface tensions of thin (1-10 nm) two-dimensional polymer or inorganic films can be used to create three-dimensional folded structures. "Molecular origami" can then be practiced in solution.

Molecular Recognition.

Any suitable molecular recognition chemistry can be used in forming the assembly. Multilayers have been successfully assembled based on electrostatic interaction, Van der Waals interaction, metal chelation, coordination bonding (i.e., Lewis acid/base interactions), ionic bonding, covalent bonding, and hydrogen bonding. The molecular recognition chemistry used preferably will have spatial requirements compatible with the polymerization technique employed. The strength of the interactions used to assemble the replicate molecules onto the template monolayer is preferably tuned both for optimal assembly (i.e., low defect density) and for convenient release of the replicate from the template.

Hydrogen bonding offers a straightforward approach. No discrete bond forming steps are needed, and dissociation of hydrogen-bonded networks may be caused by thermally heating them to disrupt the hydrogen bonds. Multilayer film assembly in accordance herewith may use hydrogen bonding of amides, carboxylic acids, and amines. Conveniently, the lattice constants of amide-containing films overlap with the lattice constants needed for diacetylene polymerization. Readily reversible covalent/coordination bonds, such as disulfides or metal chelated ensembles, may alternatively be used, with reversibility being effected by oxidation/reduction chemistry. Electrostatic/ionic bonding can also be reversibly controlled by protonation-deprotonation reactions. Multilayer films can advantageously be built up by carboxylate-amine chemistries.

Dissociation.

A variety of techniques may be employed to effect the dissociation of the replicate monolayer from the template monolayer. Controllable dissociation of the replicated monolayer from the template monolayer is preferred. Suitable dissociation mechanisms include, but are not limited to, heat (e.g., similar to DNA denaturation), sonication, irradiation, oxidation/reduction (e.g., electrochemical and reagent chemistries), pH modification, solvent exchanges (e.g., solvent polarity modification), and/or physical separation methods.

In addition, a mild "one-pot" procedure is preferred, particularly a one-pot reaction that allows the entire replicating system to be replicated many times. Controls that do not require solvent removal or reaction work-up are also preferred, such as, but not limited to, lightwave irradiation, heating, sonication, electrochemical oxidation/reduction, addition of monomer feedstock for the replication, and addition of acids or bases. Preferably, these controls are arranged so that the system can perform many replications.

As an example, a method of assembling multilayer films in one pot using hydrogen bonded assembly chemistry is simple, cost effective, and allows for the control of overall film thickness and robustness by altering the hydrogen-bonding moieties, alkyl chain lengths, and solution concentrations during the film formation step. Preferred methods for separating the replicate from the template in a hydrogen-bonded system include, but are not limited to, the use of heat, sonication, radiation, and/or solvent exchange. For example, a change in solvent polarity can be used to disrupt hydrogen bonds.

Other suitable methods of separating the replicate from the template, albeit typically less desirable, include physical stripping from a surface-fixed template. In systems involving covalent bonding between replicate and template (e.g., via disulfides or metal coordination bonds), oxidation-reduction chemistry can be used, either in an electrochemical fashion or by direct chemical oxidants/reductants. In systems involving ionic/electrostatic bonding, pH can be used as a control for splitting the replicate and template. Other methods that are used for microstructure manipulations, such as the placement of release holes within the two-dimensional structure, may also be used to facilitate the dissociation of the template from the replicate. In particular, release holes allow solvent to access interior locations within the structure, thereby increasing the likelihood of splitting two flat sheets.

Monolayer Patterning.

Any of the techniques known in the art for monolayer patterning may be used for patterning of the initial monolayer. Techniques useful in patterning a monolayer include, but are not limited to, photolithography, e-beam techniques, focused ion-beam techniques, and soft lithography. Various protection schemes such as photoresist can be used for a SAM-based system. Likewise, block copolymer patterns can be formed on gold and selectively etched to form patterns. For a two-component system, patterning can also be achieved with readily available techniques.

Soft lithography techniques are especially convenient. Ultraviolet light and a mask can be used for patterning the monomers in place, after their assembly into a monolayer. For instance, an unpatterned base monolayer may be used as a platform for assembly of the UV/particle beam reactive monomer monolayer. The monomer monolayer may then be patterned by UV photolithography, e-beam lithography, or ion beam lithography, even though the base SAM is not patterned.

Inorganics.

The present invention also allows templating of inorganic structures using replicated monolayers. Growth of inorganic colloids can be achieved by various growth mechanisms available for templated formation of inorganics on organic surfaces, such as through appropriate reduction chemistry of the desired metal salts and the use of seed or template-mediated nucleation. Using the recognition elements that provide for assembly of a second monolayer on the first, inorganic growth can be catalyzed at this interface by a variety of methods. Colloidally soluble inorganic structures can also be produced. Insulators, semiconductors, and metals, are templatable using either electroless plating techniques or mineralization.

Once the patterned monolayers have been made and replicated as many times as desired, the monolayers can be used as templates for the growth of inorganic compounds in the form of colloids bearing the shape of the patterned organic monolayer. Insulators can be patterned by carbonyl functionalities; it is well known that calcium carbonate and silica are templated by various carbonyl functionalities such as carboxylic acids and amides. By controlling the crystal growth conditions, it is possible to control the thickness and crystal morphology of the mineral growth. Titanium dioxide can also be templated.

Templated electroless plating techniques can be used to synthesize metals using existing organic functional groups. In particular, by chelating metal atoms to the carbonyl moieties of the organic replicates, electroless metal deposition can be catalyzed on these organic replicates, forming patterned metallic colloids. For instance, Cu, Au, Ni, Ag, Pd, Pt and many other metals plateable by electroless plating conditions may be used to form two-dimensional metal colloids in the shape of the organic monolayer that has been replicated. By controlling the electroless plating conditions, it is possible to control the thickness of the plated metal layer. If nanoparticles are attached to the hydrogen-bonding surface, such as, for example, covalently by chemical modification, an inorganic solid can be formed by melting the nanoparticles together. By controlling the size and thickness of the nanoparticle layer, the thickness of the sintered metal layer can be controlled. Likewise, by attaching seed nanoparticles to the organic template by hydrogen bonding, these seeds can be used as catalysts for electroless plating onto the organic template.

Carbonyl moieties may be used for templating of semiconducting materials as well, forming semiconducting colloids based on the shape of the organic replicant monolayers. Semiconductors of the II-VI type (CdSe, ZnO, and the rest of the analogs) have been reported (Saito et al., *Adv. Mater.* 14(6):

418-421 (2002)), and III-V semiconductors are also feasible, using mineralization, electroless plating, or seed mediated growth.

One major benefit of the method of the present invention is that the replicated monolayers are used as templates for inorganic structures. Additionally, by using two compatible recognition chemistries within the same monolayer, such as an amide and a carboxylic acid moiety, the growth of separate inorganic compounds and structures can be templated in whatever pattern was defined on the starting template.

Assaying a replicating organic monolayer system is a difficult task. Techniques that are suitable for assaying small quantities of shapes include AFM or cryo-TEM techniques. Growth of inorganic colloids using the organic monolayers as templates can also be a useful assay technique, allowing for a relatively straightforward examination of small evaporated aliquots of solution by, for instance, SEM, relying on a metal colloid to show up clearly by SEM. Metal colloids grown on organic monolayers also provide a better spectroscopic handle at the very low concentrations that are likely to be encountered during the early replication cycles.

Indeed, specific shapes of replicating organic monolayers, when 'developed' with a metal, can be expected to have distinct spectroscopic signatures in the UV-vis or infrared regions due to plasmon bands. For instance, colloidal silver triangles have different spectra depending on their size and quality. Such distinctive spectroscopic signatures can be used to ascertain the quality and fidelity of the replicating monolayer system, thus allowing for process optimization during replication.

In addition to replication of monolayers in solution, replication of patterned monolayers may also be conducted on a surface. Multilayer films involving insulating or semiconducting layers can be produced. Particularly, the assembly of multilayer hydrogen-bonded films of a controllable thickness can be achieved in a one-step process. By controlling the concentration of a difunctional long-chain alkyl molecule with termini that include hydrogen-bonding groups, multilayer films can be produced, the thickness of which depend on the concentration of the solution. If this approach is combined with a remotely polymerizable (UV initiated for instance) moiety in the component molecules, the resulting film so produced will generally be more robust than previous one-step methods (Miura et al., *Thin Solid Films* 393: 59-65 (2001); Viana et al., *Phys. Chem. Chem. Phys.* 3: 3411-3419 (2001)). In addition, a greater range of thicknesses (number of multilayers) should be possible.

Additionally, topochemical polymerization can aid in the monolayer assembly process itself. Since polymerization only occurs in the monolayer, monolayer formation can be triggered and promoted by exposure to UV light or polymerization catalysts. Hence, the process of monolayer formation may be kinetically speeded up since the reverse reaction (dissociation of monomer from the monolayer) is not possible once the monomer molecule has been added to a growing polymer chain. By this method, the formation of thick multilayers through hydrogen bonding interactions is made possible.

An example of the system of the present invention is illustrated in FIGS. 3A and 3B, which depict the parts of a SAM-based replication scheme. As shown in FIG. 3A, an initial monolayer 302, is patterned by a chosen technique. In the example of FIG. 3A, a thiol chain is patterned 304 on patterned gold film 304 to form a SAM 302 with amide caps 308. Initial monolayer 302 is then used as a template for the self-assembly 309 of a second monolayer 310 on top of it by molecular recognition. The initial monolayer 302 may itself be optionally polymerized 312, in order to provide better lattice matching and structural rigidity of the desired pattern. In the example shown, self-assembly step 309 is initiated by addition of a PDA precursor chain with amide cap.

Once the second monolayer 310 has formed through self-assembly, it is polymerized 316 in place. The two monolayers are then separated 318 through any suitable mechanism, such as solvent exchange or heat, to form replicate 320 of the original monolayer 302. Both replicate 320 and the original monolayer 302 can now function as templates for monolayer assemblies 330, 332. As depicted in FIG. 3B, the process can be repeated many times, forming an exponential replication system.

A preferred embodiment of the example system illustrated in FIGS. 3A and 3B utilizes diacetylene polymerization. The lattice constants appropriate for the polymerization, the amide hydrogen bonding space requirements, and the thiol-gold contact spacing all fall within essentially the same range, which is preferred. Thus, the spatial requirements of the polymerization reaction and molecular interactions (e.g., hydrogen bonding, electrostatic or covalent interactions) overlap. For a Langmuir-Blodgett-based system, there is no issue with the underlying substrate, which also needs to be lattice matched.

FIG. 4 depicts exemplary target molecules (in this case, for C9 chains) designed for use in the system illustrated in FIGS. 3A and 3B. In general, the number of methylene linker carbons 402 used as spacers between the polymerizable moieties 410 and the recognition elements 420 can be quite varied, being typically in (but not limited to) a range of 1 to 20. Thus, in the exemplary molecules of FIG. 4, any entity labeled "C" followed by a number (referring to the number of methylene units) may be varied in order to construct different target molecules suitable for use in the present invention.

Molecules 401, 441, 451, 461 are intended to be used for the formation of a patterned template SAM on a gold surface, and allow for the use of either amide or carboxylate hydrogen bonding as the organizing principle for templated replication. In particular, molecules 401, 441 incorporate a polymerizable diacetylene unit, which may be beneficial in locking in the desired lattice constants and ordering within the base SAM template. However, molecules 451, 461 may work just as well for the formation of a base SAM patterned template, and polymerization is not required. Ending unit 430 will be bound to the gold surface in a SAM, and will not interfere with the monolayer templating effect.

Molecules 411, 421, 431 are potential replicating monomers. Molecules 421, 431 have two polymerizable units 410 in the chain, allowing for thorough cross-linking of the monolayer. The family of replicating monomers exemplified by molecule 431 (Hentriaconta-11,13,20,22-tetraynoic acid) and by molecule 421 (Hentriaconta-11,13,20,22-tetraynoic acid amide) is particularly desirable for this invention. Also useful are Triaconta-10,12,19,21-tetraynoic acid amide and Triaconta-10,12,19,21-tetraynoic acid. A family of molecules which are especially useful for the invention is therefore defined as molecules of the type of molecule 431 (Hentriaconta-11,13,20,22-tetraynoic acid) or molecule 421 (Hentriaconta-11,13,20,22-tetraynoic acid amide), which have two diacetylene units linked by a methylene chain of from 1 to 20 carbons to form a bis(diacetylene) unit, and which have an alkyl chain of from 1 to 20 carbons terminating in an inert functionality such as a methyl on one end of the bis(diacetylene) unit, and which have an alkyl chain of from 1 to 20 carbons terminating in an amide or carboxylic acid at the other end of the bis(diacetylene) unit.

While in the embodiment shown molecular recognition between monolayers is achieved by the bonding between amide functionalities or the bonding between carboxylic acid functionalities, many other functionalities may be advantageously utilized in the present invention. Certain other suitable functionalities may require additional components and/or additional steps in the replication process that are apparent to one of skill in the art.

FIG. 5A depicts a generic self-replicating monomer unit, of which the molecules in FIG. 4 are specific examples. In FIG. 5A, ending unit Z 502 for the monomer chain may be -methyl, a functionality designed to affect the solubility of the monomer or resulting colloidal shape (such as, for example, $-CH_2OH$), $-CH_2OBn$, $-NMe_2$, or any other group that will not interfere with the recognition chemistry. Ending unit Z 502 is attached by methylene repeats m 504 to polymerizable moiety Polym 510. Polymerizable moiety Polym 510 may be a single polymerizable unit, but preferably contains two polymerizable units separated by some number of methylenes. Polymerizable units such as diacetylenes, olefins, or dienes are particularly suitable.

Polymerizable moiety Polym 510 is further attached by methylene repeats n 514 to recognition chemistry Recog 520. Methylene repeats m 504, n 514 are used for increasing order and van der Waals interactions in a SAM. Recognition chemistry Recog 520 may be based on any suitable chemistry, including, but not limited to, hydrogen bonding, such as amide-amide bonding, or more complex hydrogen-bonding patterns, such as barbituric acid or diaminotriazine. Whatever the choice for recognition chemistry Recog 520, the template must display a complementary recognition element. The recognition element must be self-complementary unless there is a set of two replicating monomers.

Figure 5B:
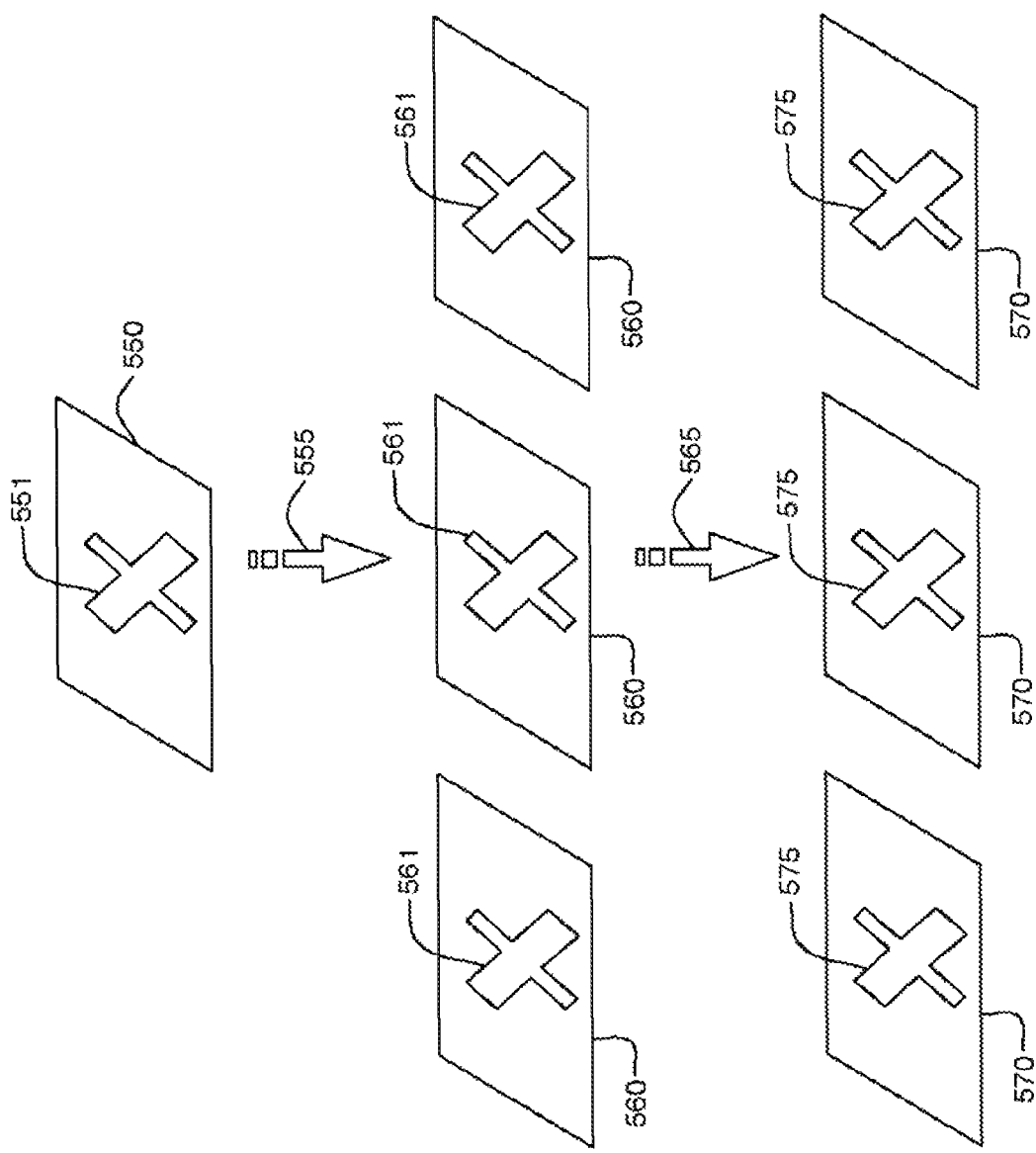
FIG. 5B illustrates a two-component replication system according to an embodiment of the present invention.

FIG. 5B depicts an exemplary two-component replication system utilizing two different kinds of recognition chemistries (i.e., the monolayer is composed of two chemically compatible molecules). In FIG. 5B, initial template monolayer 550 containing component A, which contains a pattern of component B 551 within it, undergoes replication cycles 555, maintaining the two-dimensional segregation of replicating monomers 560, 561 (for two different types of replicating monomer units with compatible cross-linking chemistry). After replication, selective mineralization and/or electroless plating 565 produces a two-dimensional inorganic sheet 570 with patterned domains 575 within it.

One suitable system utilizes two different recognition chemistries in the diacetylene system, amide-based and carboxylic acid-based. Since these systems have very similar lattice constants, they can form the basis of a self-replicating system composed of two components. During subsequent replications, the carboxylic acid domains and the amide domains experience little or no mixing, allowing the two-component, patterned assembly to be exponentially replicated. Use of a metal ion to chelate to the carboxylate moiety may be useful in keeping the two components well segregated during replication cycles, maintaining the pattern integrity within the assembly.

More than two chemically compatible molecules may be used in monolayer synthesis. Patterning of the initial template can occur according to the defined regions of the two or more molecules composing the monolayer. After replication is complete, the two component replicates can then be mineralized or electroless plated in a way that maintains the pattern of the replicants, creating opportunities for making two component inorganic colloids that are patterned.

An alternate embodiment of the present invention provides a replicating system wherein the replicating monomer is not necessarily self-complementary. In this case, there is no pattern in the monolayer to be replicated, but there are two types of monolayers in the system, each of which are composed of different monomers. In an example implementation, a monomer with Adenine as the recognition element forming the basis of a monolayer template (to use DNA as a simple example) is paired with another monomer terminating in Thymine (the H Bond partner of Adenine in DNA) in order to replicate this monolayer. This provides one template terminating in Adenines, and another one terminating in Thymines after disassociation. The system of this embodiment is therefore capable of self-replication, but requires two separate monomers present at once (typically in equal amounts).

Replication System Based on Nanoparticles.

Figure 6A:
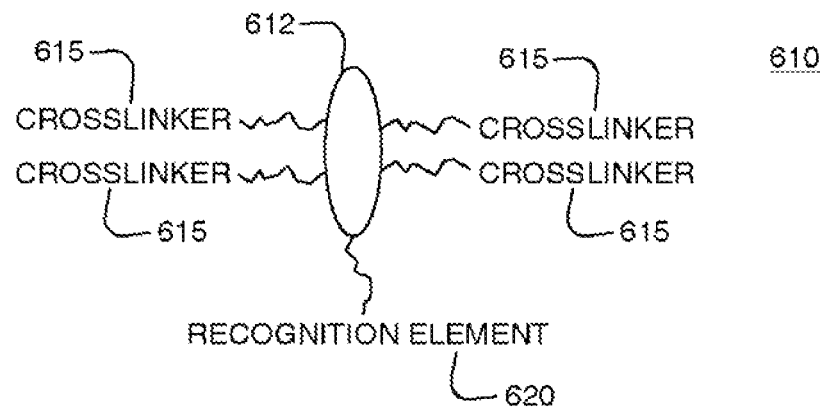
FIGS. 6A-B depict generalized replicating monomer units assembling on a template according to an embodiment of the present invention.
Figure 6B:
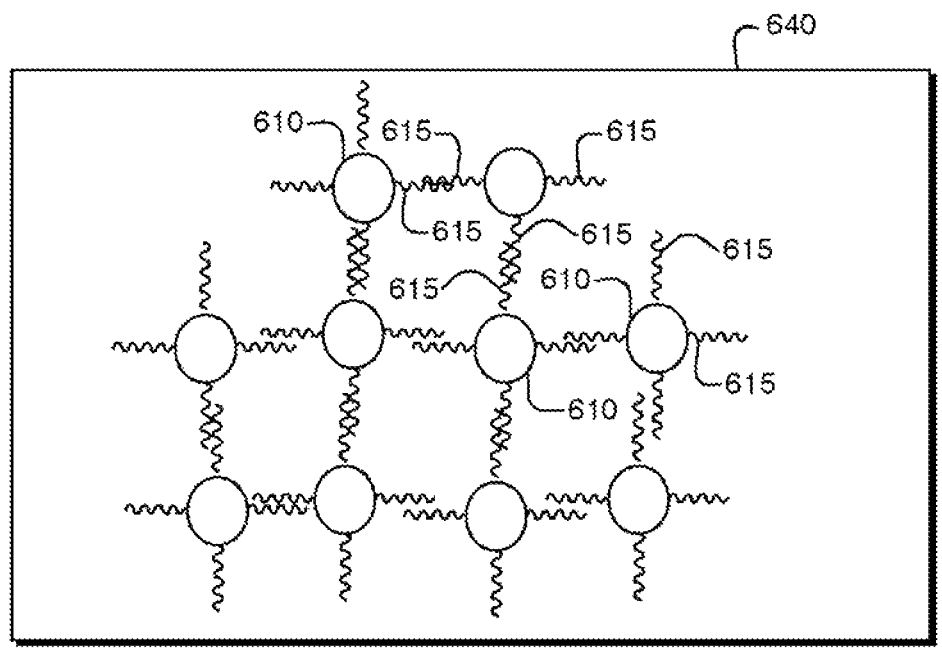

The present invention may be extended to replication of two-dimensional assemblies of nanoparticles, an example that is also instructive as to the requirements for replication of monolayers according to the present invention. The basic requirements of a replication system based on nanoparticles are depicted in FIGS. 6A-B. The key component of the replicating system is generalized replicating monomer unit 610. Choices regarding patterning to form the initial template, as well as the replication cycle, are determined at least in part by the make-up of replicating monomer unit 610.

As shown in FIGS. 6A-B, monomer unit 610 is built on inorganic or organic nanoparticle 612 to which multiple Crosslinkers 615 are attached. The number of Crosslinkers 615 attached to nanoparticle 612 may vary, but monomer unit 610 should have the ability to cross-link with more than 2 adjoining monomer units in the two-dimensional matrix. In addition, monomer unit 610 must incorporate Recognition Element 620 capable of binding to template 640 reversibly (yet strongly enough to form a complete monolayer on the template), in order that a replication cycle can be performed. As multiple replicating monomer units 610 assemble on template 640 in the xy plane, it is important that they be able to crosslink 615 in multiple directions and not just form chains. This allows formation of a robust sheet that replicates the pattern.

An additional desirable property of the monomer unit, though not strictly necessary for replication, is that polymerization of the monomer takes place predominantly when it is bound to the template. In other words, unproductive polymerization of the replicating monomer unit, such as that which takes place in solution away from the 2-D template, is desirably minimized, preferably having a very low rate relative to the rate of the desired polymerization reaction that occurs when the monomer is bound to the template. This eases purification of the replicated structures, and makes for more efficient use of the replicating monomer. Minimization of unwanted polymerization helps to make the system of the present invention a practical replication system.

Topochemical polymerization is a very useful reaction in this context, because it helps ensure that polymerization occurs exclusively on the surface where the monomers can form an organized array resembling the solid state. Groups that perform topochemical polymerization, such as diacetylenes or butadienes, can thus be used as linkers. However, polymerizations that can be speeded up by many orders of magnitude due to proximity effects on the template are also useful. These may involve a two-member set of replicating monomer units.

Figure 7A:
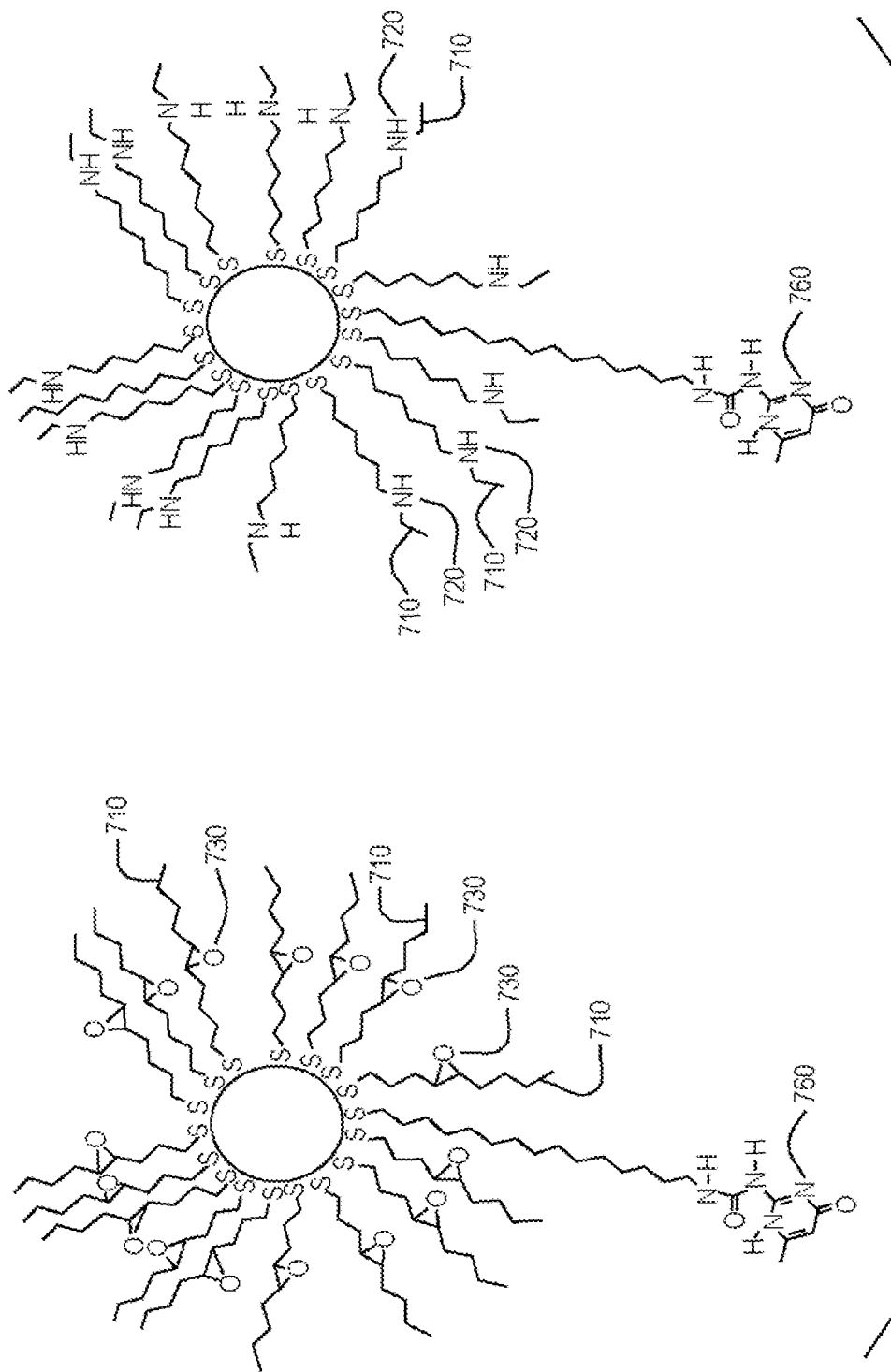

For example, one of the monomers (A) may possess epoxides or other relatively electrophilic moieties within the ligand shell of a nanoparticle, as seen in FIGS. 7A-B. The other monomer unit (B) then should possess nucleophilic moieties within its ligand shell that are expected to react with monomer (A) upon close proximity. However, such reaction is normally slow when the two monomers are simply dissolved in the same solution. Only when they enter a phase involving intimate contact and close packing (such as occurs within a monolayer) do these groups react. There is some precedent for this application within the realm of nanoparticle chemistry, as it is often the case that nanoparticles are stable in solution but irreversibly agglomerate in the solid phase (Leff et al., *Langmuir* 12: 4723-4730 (1996)). Both monomers (A) and (B) contain the same recognition chemistry, and distribute evenly across a template surface, giving on average an ensemble mixture of (A) and (B) which may form a crosslinked sheet.

FIGS. 7A-B depict an especially robust four-hydrogen bond self-complementary recognition motif that is useful for large replicating monomers. In FIG. 7A, methylene chains 710 shield electrophilic amines 720 from epoxide units 730 while in the solution phase. As seen in FIG. 7B, once on template 750 with exposed quadruple hydrogen-bonding groups 760, methylene chains 710 intercalate, and amines 720 and epoxides 730 react to create a crosslinked sheet.

Nanoparticles that are monofunctionalized regarding the recognition element are important for this type of a self-replicating monolayer system. If the replicating monomer nanoparticles are not monofunctionalized with regards to the recognition element, forming multilayers and/or polymeric chains of the replicating monomers will become problematic due to unwanted cross-linking. The patent family of Hainfeld et al (U.S. Pat. No. 5,521,289, Hainfeld et al. (1996); U.S. Pat. No. 6,121,425, Hainfeld et al. (2000)) discloses methods for making monofunctionalized nanoparticles that involve HPLC purification and various precipitations. Various statistical methods can also be envisioned for obtaining monofunctionalized nanoparticles (which can otherwise be fully functionalized with the cross-linking ligands). Other suitable methods for making monofunctionalized nanoparticles are described in co-pending U.S. patent application Ser. No. 10/621,790, ("Nanoparticle chains and preparation thereof", Jacobson et al., Jul. 17, 2003).

Figure 8:
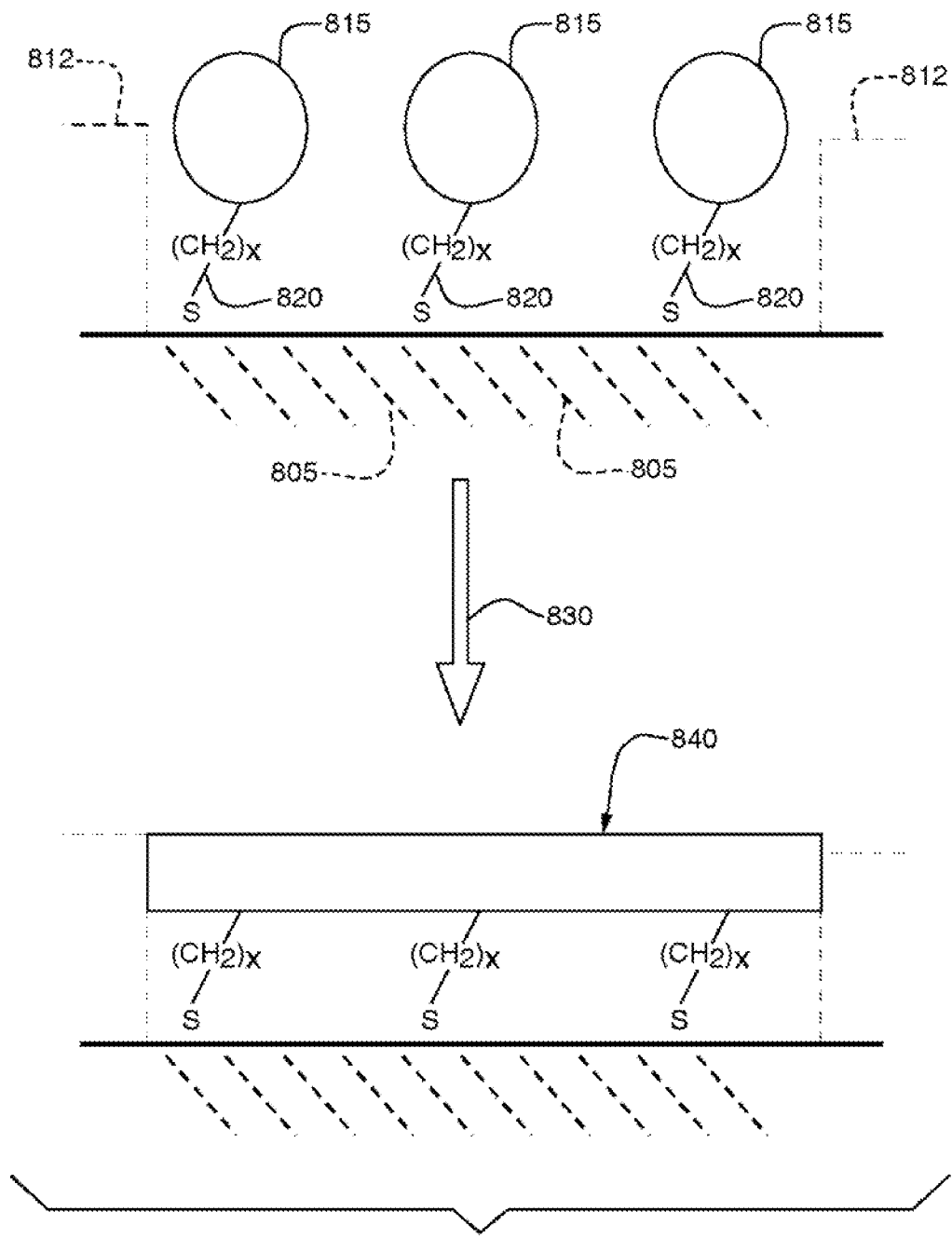
FIG. 8 illustrates surface pattern recognition with nanoparticles according to an embodiment of the present invention.

FIG. 8 depicts an exemplary embodiment of the method of the present invention, achieving replication of a structure patterned on gold. The method of FIG. 8 includes forming gold patterns 805 on a surface 810 by patterning with, for example, photoresist and then exposing the underlying gold surface. Boundaries 812 formed by photoresist define the shape to be replicated. Thereafter, nanoparticles 815 (formed from Au, Ag, or other elements) are anchored to the patterned gold surface via thiol linkages 820 or some other recognition element. Upon heat curing, the nanoparticles can be melted or sintered together 830, forming a solid sheet replicate 840 of the patterned gold, having a thickness approximately half the diameter of starting nanoparticles 815.

Alternatively, solution stable nanoparticles that agglomerate in the solid phase can be used, so long as they are monofunctionalized with a recognition moiety having reversible binding. This provides a relatively simple replicating unit. After sintering or agglomeration on the 2-D template, the replicate is then separated from the surface by thermal energy or mechanical energy, for instance by heating in a solvent or mechanical stripping. The replicant may then itself be used as a template for further replication.

Sintering of nanoparticles is one technique known for producing patterns on a surface (Fullam et al., *Adv. Mater.* 12: 1430-1432 (2000); U.S. Pat. No. 6,294,401, Ridley et al. (2001); Wuelfing et al., *Chem. Mater.* 13: 87-95 (2001)). A variety of capping groups and elemental compositions can be used to help determine the sintering conditions needed. Nanoparticles also spontaneously "melt" when the capping groups are removed, so more labile capping groups such as amines on gold may be used to facilitate formation of gold films. A replication system based on nanoparticle sintering or melting can thus be designed to allow exponential replication.

Further Specific Examples, Embodiments and Synthesis Methods.

Figure 9:
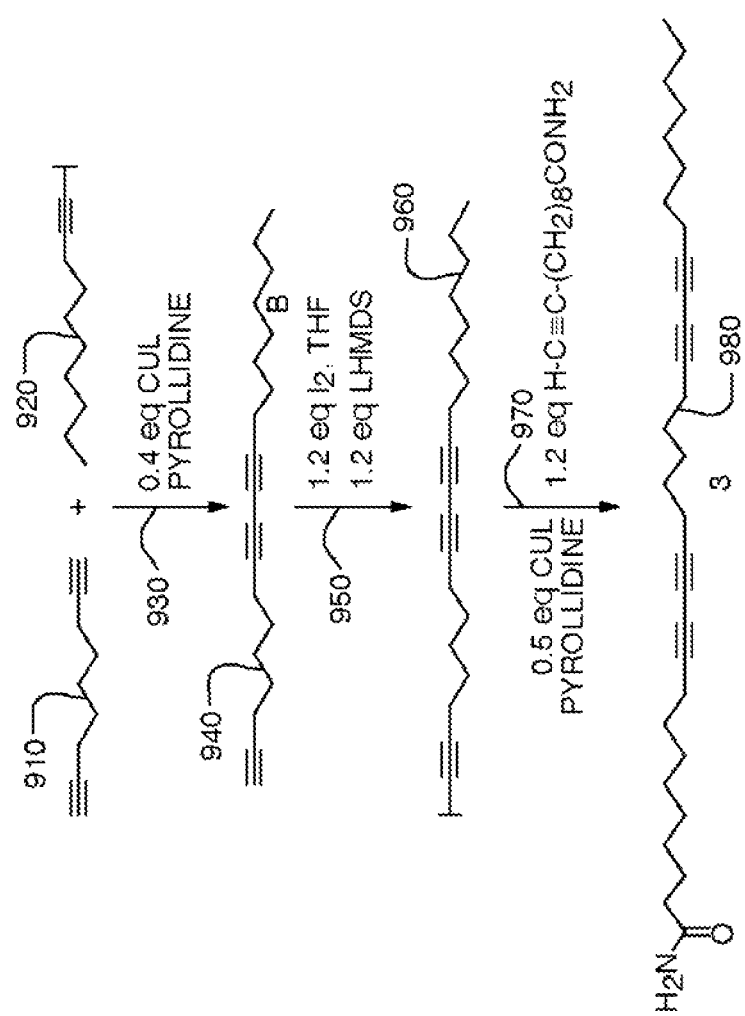
FIG. 9 depicts synthesis of a BisDA replicating monomer according to an embodiment of the present invention.

The synthesis of the BisDA replicating monomer 980 was carried out using Cadiot-Chodkiewics coupling chemistry, as is shown in FIG. 9. The Cadiot-Chodkiewics couplings using amines as solvents were found to be far more effective for these compounds than the traditional reagent set. (Alami et al., *Tet. Lett.* 37(16): 2763-5 (1996)) Molecule 910 1,8-Nonadiyne is commercially available. Molecule 920 1-iodo-1-decyne (Narayana, Rao et al. 1995) has been previously synthesized. Using cuprous iodide and pyrollidine as solvent, these were coupled to produce molecule 940. Molecule 940 was then lithiated to produce molecule 960. Molecule 960 may then be coupled using cuprous iodide and pyrollidine with 10-undecynoic acid amide to yield molecule 980. 10-Undecynoic acid amide (Crisp et al., *Tetrahedron* 53(4): 1505-1522 (1997)) has been previously synthesized as well. The bis(diacetylene) 980 is quite labile to heat and light in the solid state or on silica gel, so it is stored in a methylene chloride solution at liquid nitrogen temperatures. Full synthetic details follow. Included is a synthesis of 11-dodecynoic acid amide, which can be substituted in step 970 of FIG. 9 to result in the bis(diacetylene) replicating monomer 421 shown in FIG. 4.

Synthesis of molecule 16-mercaptohexadecanamide, similar in function in the context of the present invention as molecule 461 of FIG. 4, was achieved by the method reported by Nuzzo and coworkers (Nuzzo et al., *J. Am. Chem. Soc.* 112: 558-569 (1990)). This molecule was used to create a base SAM template for replication of monomer 980.

11-dodecynoic Acid Amide (an Alternate Chain for Building the BisDA Replicating Monomer) 421.

11-Dodecyne nitrile (3.936 g, 22.2 mmol) and potassium carbonate (0.441 g, 3.19 mmol) were added to a flask and inerted with nitrogen, followed by the addition of 6.7 mL of DMSO. The flask was cooled in an ice bath and 2.7 mL of 30% $H_2O_2$ was added slowly via syringe. The reaction was allowed to warm to room temperature and stirred overnight. Additional hydrogen peroxide can be added if the reaction shows remaining starting material. The reaction was diluted with 100 mL of diethyl ether and worked up by extraction with 1 M HCl (3×80 mL), and with water (3×80 mL). The organic phase was dried over $MgSO_4$ and concentrated in vacuo to yield 2.352 g of pure A. 54% yield; $^1$H NMR ($CDCl_3$) δ 5.55 (s, 2H, $NH_2$), 2.18 (m, 4H, $CH_2$—C≡C & $CH_2$—CO), 1.92 (t, J=2.4 Hz, 1H, H—C≡C), 1.61 (m, 2H, $CH_2$—C—CO), 1.49 (m, 2H, $CH_2$—C—C≡C), 1.26 (m, 10H, $CH_2$ chains); MS (ESI) [M+Na]$^+$ calc. 218.1515. Found 218.1516. Elemental analysis calc. for $C_{12}H_{21}NO$: C, 73.80; H, 10.84; N, 7.17. Found: C, 74.14; H, 10.99; N, 7.54.

Nonadeca-1,8,10-triyne (940)

Pyrollidine (20 mL) and CuI (0.65 g, 3.42 mmol) were added to a nitrogen flushed reaction vessel. Nona-1,8-diyne (1.58 g, 13.17 mmol) was added via syringe. 1-Iodo-1decyne (2.26 g, 8.53 mmol) was added via syringe dropwise to the solution over ten minutes. The reaction was stirred under nitrogen for 24 h. The reaction mix was then quenched with ammonium chloride (10 mL), separated with diethyl ether, and dried with anhydrous magnesium sulfate. Nonadeca-1,8, 10-triyne was then isolated using silica column chromatography with a 1% ether/hexane eluting solution obtaining 1.06 g of an oil. 50% yield; $^1$H NMR ($CDCl_3$) δ 2.29 (m, 4H, CH$_2$—C≡C), 2.22 (dt, 2H, CH$_2$—C≡C, J=7, 2.7 Hz), 1.97 (t, 1H, H—C≡C, J=2.7 Hz), 1.54 (m, 6H, CH$_2$—C—C≡C), 1.33-1.40 (sextuplet, 2H, CH$_2$—CH$_2$—CH$_3$), 1.27 (m, 10H, C—CH$_2$—C), 0.88 (t, 3H, CH$_3$); $^{13}$C NMR (CDCl$_3$) δ: 84.62, 77.99, 77.36, 68.63, 65.76, 65.45, 32.21, 29.54, 29.46, 29.25, 28.72, 28.34, 28.31, 28.23, 23.06, 19.61, 19.52, 14.53; MS (ESI) [M+Na]$^+$ calc. 279.2083. Found 279.1723 (very unstable to any MS technique). Elemental analysis calc. for C$_{19}$H$_{28}$: C, 88.99; H, 11.01. Found: C, 88.80; H, 10.96.

1-Iodo-nonadeca-1,8,10-triyne (960).

Nonadeca-1,8,10-triyne (0.802 g, 3.133 mmol) and anhydrous THF (96 mL) was cooled to −78° C. in a dry flask under nitrogen. LiN[Si(CH$_3$)]$_2$ (LHMDS) in THF (3.76 mmol) was added to the reaction mix slowly via dry syringe. In a separate flask I$_2$ (9.55 g, 3.76 mmol) was dissolved in dry THF (20 mL). The iodine solution was added dropwise to the nonadeca-1,8,10-triyne solution until reaction completion (notably becoming orange-red). The reaction was stirred for 30 min, and slowly warmed to room temperature. The reaction was extracted with diethyl ether and 1M K$_2$S$_2$O$_3$. The organic phase was dried over anhydrous MgSO$_4$, and concentrated by evaporation to yield 1-iodo-nonadeca-1,8,10-triyne (0.93 g, 2.45 mmol). GC/MS showed no starting material remaining 79% yield; $^1$H NMR (CDCl$_3$) δ 2.15-2.33 (m, 6H, CH$_2$—C≡C), 1.48 (m, 6H, CH$_2$—C—C≡C), 1.33-1.39 (m, 2H, CH$_2$—CH$_2$—CH$_3$), 1.28 (m, 10H, C—CH$_2$—C), 0.85 (t, 3H, CH$_3$).

Triaconta-10,12,19,21-tetraynoic acid amide (BisDA) (980).

CuI (0.126 g, 0.66 mmol) and 10-undecynoic acid amide (0.29 g, 1.59 mmol) were added to a flask and inerted with nitrogen. Pyrollidine (5 mL) was then added. In a separate flask 1-Iodo-nonadeca-1,8,10-triyne (0.5 g, 1.3 mmol) was mixed with pyrollidine (5 mL) and subsequently added slowly to the amide solution. The reaction mix was left in darkness under nitrogen for 48 hours, then quenched with aqueous 1M NH$_4$Cl (10 mL), and worked up with CH$_2$Cl$_2$ and 1 M HCl. The organic was dried over anhydrous MgSO$_4$. Organic products were concentrated by rotary evaporation, although polymer formed, decreasing yield. Hexanes trituration removed unreacted 1-Iodo-nonadeca-1,8,10-triyne. Desired product was obtained by several crystallizations from hexanes/ethyl acetate, again under dark conditions. All handling of the solid was done under red light. Final product triaconta-10,12,19,21-tetraynoic acid amide was made up of white crystals (0.377 g, 0.86 mmol) and was stored frozen (liquid nitrogen) in methylene chloride. 65% yield; $^1$H NMR (CDCl$_3$) δ: 5.31 (s, 2H, NH$_2$), 2.22-2.26 (m, 10H, CH$_2$—C≡C & CH$_2$—CO), 1.58-1.66 (quin, 2H, J=7, CH$_2$—C—CO), 1.45-1.56 (m, 8H, CH$_2$—C—C≡C), 1.28-1.4 (m, 20H, C—CH$_2$—C), 0.86-0.91 (t, 3H, CH$_3$); $^{13}$C NMR (CDCl$_3$) δ 175.69, 77.98, 77.84, 77.34, 65.69, 69.45, 65.37, 57.68, 53.63, 38.37, 38.35, 33.80, 32.97, 32.92, 32.03, 29.34, 29.27, 29.07, 28.94, 28.55, 28.47, 28.26, 28.26, 28.06, 27.17, 25.67, 22.86, 19.39, 19.32 14.30. MS (ESI) [M+H]$^+$ calc. 436.3574. Found 436.3560.

Formation of a Patterned Monolayer Template Utilizing Amide Hydrogen Bonding, Followed by Formation of the First Replicate.

Patterning and formation of an initial template for replication using the replicating monomer triaconta-10,12,19,21-tetraynoic acid amide (BisDA 980) can be performed as follows. An ultraflat gold substrate is prepared by a template stripping technique. The substrate is immediately stamped with a patterned poly(dimethylsiloxane) stamp which has been wet-inked or contact-inked with octadecanethiol (Libioulle et al., *Langmuir* 15: 300-304 (1999)). After stamping, the substrate is immersed into a solution of 0.1 mM 16-mercaptohexadecanamide in ethanol for 4 hours. The substrate is then transferred to a solution of 0.25 mM BisDA (in decalin, under low light conditions).

The substrate is soaked in the solution of BisDA in darkness for 12-16 hours. Upon removal of the substrate, it is blown dry with nitrogen, but not rinsed. Areas of the substrate exclusively covered with a bis(diacetylene) adlayer dewetted. The substrate is then polymerized in a nitrogen atmosphere for 2 minutes using a UV pen lamp at 254 nm, forming a cross-linked replicate of the template pattern. The amount of UV exposure is important for proper cross-linking of the replicate structure. Two minutes is at the lower end of the preferred exposure time, while 60 minutes is at the upper end. In addition, the degree of order in the patterned template monolayer is critical. The higher the degree of order, the better the replicate monolayer forms and is polymerized. The degree of order for both the template monolayer and the replicate monolayer can be judged by contact angle, ellipsometry, and grazing angle FTIR among the typical techniques.

The solvent used for formation of the pre-polymerized replicate/template structure (often called an adlayer structure in the literature) is important. Non-hydrogen bonding solvents are preferred when using the BisDA system. Solvents such as decalin (decahydronapthalene) form the pre-polymerized adlayer structure quite well. Other similar solvents, such as hexadecane and dodecane will also be expected to perform similarly. In addition, comixtures of decalin and toluene with ratios up to 1:3 decalin:toluene have been found to produce polymerizable adlayer structures. Other mixtures of solvents that allow for the desired hydrogen bonding interaction in the case of the BisDA molecule and similar molecules are included as possible solvents for use during replication cycles.

Using soft lithography, templates with features of many microns down to 100 nm are accessible. For very small templated shapes and features, an alternate fabrication technique may be needed due to difficulties with alkyl thiol ink diffusion. Also, alkyl thiol ink diffusion may create some disorder at the edges of a given pattern, decreasing the resolution of a replicate monolayer. An approach based on an inorganic e-beam resist, such as HSQ, should make it possible to directly fabricate thiol patterns with very small features on ultraflat gold.

Liftoff or 'Melting' of the First Replicate.

The patterned replicate monolayers are themselves soluble and can be used to begin replication cycles in solution, away from the patterned surface. For instance, the shapes can be lifted off from the substrate in polar solvents that are capable of solubilizing the replicate monolayers, which have alkyl groups on one side and amide groups on the other side. The monolayer sheets in the case of BisDA are approximately 2.5 nm thick, as judged by ellipsometry measurements on a surface. These monolayer sheets may or may not remain flat when they are solubilized, and their degree of curvature and aggregation will be dictated by the solubility parameters of the solvent in which they are dissolved. Appropriate solvents for the shapes include warm chloroform and N-methyl-pyrrolidinone. Further solvents with similar solubility characteristics are also appropriate for solvation, such as, but not limited to, dichloroethane and other halogenated solvents, and the large family of dipolar aprotic solvents which are well known to disrupt hydrogen bonding (for example dimethylsulfate, hexamethylphosphoramide, dimethylformamide, N,N-dimethyl acetamide). Solvation of replicated monolayer structures will also depend in large part on the size and shape of the pattern. Larger micron and higher-sized patterns may be more prone to aggregation that will inhibit further replication cycles. Smaller patterns below 1 micron in size will be more soluble and easier to replicate.

Solution Replication of Monolayer Patterned Shapes.

Replication chemistry is preferably conducted in fluorinated labware to prevent loss of replicated monolayers due to surface adhesion. In general, the replication system is kept in darkened conditions to ensure that unnecessary degradation of the replicating monomers or monolayers does not occur. A solvent such as decalin is used for chelation of the replicating monomers to the template monolayers. The solution is exposed to UV light, 254 nm. In order to separate the replicated monolayer from the template monolayer, several options exist depending on the size of the replicated shape/pattern. Heating of the decalin solution may suffice. Addition of more replicating monomer, so that it breaks apart the two monolayer sheets, may also be useful. Solvent addition in the form of a volatile chlorinated solvent, such as chloroform or methylene chloride, combined with heating, may further be a useful technique. Or a combination of these options may be necessary, again depending on the size of the replicated pattern. Upon starting the next replication cycle, removal of any added chlorinated solvent can be accomplished by vacuum evaporation, since decalin has a much lower volatility than a solvent such as chloroform.

Monitoring of replication cycle progress can be assayed in many ways. Since the BisDA monomer forms a polymer sheet with a high absorption coefficient in the visible light region, simple UV-vis monitoring may be useful. In addition, assays based on taking aliquots can be used. An aliquot may be analyzed by AFM (contact, non-contact, tapping, either after drying the aliquot or in the solution phase). Alternatively, cryo-TEM techniques based on a flash freeze and metal evaporation at liquid nitrogen temperatures or mass spectrometry techniques can be used. A technique based on electroless plating or immunogold-silver plating can be used for either TEM or SEM evaluation.

Preparation of Ultraflat Gold Substrates.

Ultraflat template stripped gold substrates are fabricated using mica from SPI (grade V-4 muscovite) as follows. 150 nm of gold is e-beam evaporated at 2 A°/sec onto freshly cleaved mica, followed by 50 nm of titanium at 2-3 A°/sec, as monitored by QCM. The e-beam chamber is typically at $3*10^{-6}$ torr, with no temperature control on the substrates. These gold substrates are then coated with a layer of spin-on-glass to prevent alloying of indium with the titanium and gold. Filmtronics SOG 20B is applied by static dispensing, followed by spinning at 2000 rpm for 30 seconds. The substrates are soft-baked at 80, 150, and 250° C. for one minute each. The substrates are then immediately placed upside down onto a glass slide covered with molten indium at 250° C. on a hot plate. For 1.4 cm² mica substrates, a 1 cm² piece of 10 mil thick indium foil is more than adequate. The mica is pressed firmly down with a hot weight to form an indium/gold/mica sandwich. After 1-2 min, the substrates are set aside to cool, and can be stored until needed. The sandwich can be cleaved by placing it in hot DI water (80-100 C) for about 10 minutes. Trimming a side of the mica aids this process, thus ensuring that one edge is not 'sealed' by indium or spin-on-glass. The gold surfaces thus produced have RMS roughness values of 0.35-0.45 nm as measured by AFM.

The apparatus and method of the present invention, therefore, provide a self-replicating monolayer system. The present invention features techniques that may be advantageously employed for making nanostructures of sizes from about 2 nm to about 1000 nm. The method of the present invention is highly controllable, can be used to replicate patterns over many generations, and is preferably, though not required to be, a "one-pot" process producing monolayers that are specifically cross-linked or patterned. In one particular embodiment, the system of the invention utilizes polymerization of a nanoparticle ensemble using a lithographically-defined template. Another particular embodiment of the present invention provides a method for synthesis of two-dimensional lithographically defined single molecule polymers that can be readily suspended in a solvent. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications and substitutions by one of ordinary skill in the art are therefore also considered to be within the scope of the present invention, which is not to be limited except by the claims that follow.

What is claimed is:

1. A method for replicating a monolayer, comprising the steps of:
    forming a first type of template from a subset of a first set of monomers having a first recognition chemistry;
    binding a subset of a second set of monomers having a second recognition chemistry to the first type of template to form a monolayer replicant of a first replicant type, the second recognition chemistry being complementary to the first recognition chemistry;
    polymerizing the monolayer replicant of a first replicant type;
    disassociating the polymerized monolayer replicant of a first replicant type from the first type of template; and
    forming at least one replicated monolayer by binding monomers from the first set of monomers to a second template type comprising the polymerized monolayer replicant of a first replicant type.

2. The method of claim 1, wherein the monomers are nucleotides, oligonucleotides, or amino acids.

3. The method of claim 1, wherein the monomers are nanoparticle ensembles.

4. The method of claim 1, wherein the monomers contain at least two reactive functional groups.

5. The method of claim 1, wherein the monomers contain a terminus bearing one or more molecular recognition elements.

6. The method of claim 1, wherein the monomers are selected from the group consisting of Hentriaconta-11,13,20,22-tetraynoic acid, Hentriaconta-11,13,20,22-tetraynoic acid amide, Triaconta-10,12,19,21-tetraynoic acid amide, and Triaconta-10,12,19,21-tetraynoic acid.

7. The method of claim 1, further including the step of disassociating the replicated monolayer from the template of a second template type.

8. The method of claim 1, further including the step of growing an inorganic structure upon the replicated monolayer.

9. The method of claim 1, further including the step of selective mineralization of the replicated monolayer.

10. The method of claim 1, further including the step of electroless plating of the replicated monolayer.

11. The method of claim 1, further including the steps of nanoparticle adhesion to, and sintering of, the replicated monolayer.

12. A method for replicating a pattern, comprising the steps of:
providing a plurality of sets of monomers, each set of monomers having a recognition chemistry;
providing a template having a plurality of regions, the template being complementary to the pattern to be replicated and each region of the template being complementary to a different one of the sets of monomers;
binding a subset of one of the sets of monomers to each region according to said recognition chemistry, forming a replicate of the pattern;
polymerizing the replicate of the pattern; and
disassociating the polymerized replicate of the pattern from the template.

13. The method of claim 12, further including the step of binding a plurality of inorganic materials to the replicate of the pattern.

14. The method of claim 13, wherein at least one of the inorganic materials is metallic.

15. The method of claim 12, further including the step of selective mineralization of the replicate of the pattern.

16. The method of claim 12, further including the step of electroless plating of the replicate of the pattern.

17. The method of claim 12, further including the step of growing a semiconductor upon the replicate of the pattern.

18. The method of claim 12, wherein the monomers are nucleotides, oligonucleotides, amino acids, or nanoparticle ensembles.

19. The method of claim 12, wherein the monomers contain at least two reactive functional groups.

20. The method of claim 12, wherein the monomers contain a terminus bearing one or more molecular recognition elements.

* * * * *